US011612378B2

(12) United States Patent
Seitel et al.

(10) Patent No.: US 11,612,378 B2
(45) Date of Patent: Mar. 28, 2023

(54) MOUNTING DEVICE FOR REVERSIBLY MOUNTING AN ELECTROMAGNETIC FIELD GENERATOR ON AN ULTRASONIC PROBE

(71) Applicant: Deutsches Krebsforschungszentrum, Heidelberg (DE)

(72) Inventors: Alexander Seitel, Heidelberg (DE); Alfred Franz, Westerstetten (DE); Lena Maier-Hein, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 50 days.

(21) Appl. No.: 16/606,417

(22) PCT Filed: Apr. 18, 2018

(86) PCT No.: PCT/EP2018/059886
§ 371 (c)(1),
(2) Date: Oct. 18, 2019

(87) PCT Pub. No.: WO2018/192964
PCT Pub. Date: Oct. 25, 2018

(65) Prior Publication Data
US 2020/0187900 A1 Jun. 18, 2020

(30) Foreign Application Priority Data
Apr. 19, 2017 (EP) .................. 17167015.1

(51) Int. Cl.
*A61B 8/00* (2006.01)

(52) U.S. Cl.
CPC .......... *A61B 8/4227* (2013.01); *A61B 8/4444* (2013.01)

(58) Field of Classification Search
CPC ........................ A61B 8/4277; A61B 8/4444
See application file for complete search history.

(56) References Cited

U.S. PATENT DOCUMENTS 7,926,776 B2    4/2011  Cermak
9,597,008 B2 *  3/2017  Henkel ............... H01F 7/0273
(Continued)

FOREIGN PATENT DOCUMENTS

DE  202015104277 U1 *  8/2015  ........... A61B 8/4209
JP  2005-279096 A     10/2005
(Continued)

OTHER PUBLICATIONS

März et al., Mobile EM Field Generator for Ultrasound Guided Navigated Needle Insertions, Information Processing in Computer-Assisted Interventions, Jun. 2013, vol. 7915, 115 pages.
(Continued)

*Primary Examiner* — Boniface Ngathi N
(74) *Attorney, Agent, or Firm* — Taft Stettinius & Hollister LLP

(57) ABSTRACT

A mounting device for reversibly mounting at least one electromagnetic field generator on an ultrasonic probe for orientating the electromagnetic field generator with respect to the ultrasonic probe in at least one mounting position is disclosed. The mounting device comprises at least one first fastening structure. The mounting device is connectable to the electromagnetic field generator via the first fastening structure.

21 Claims, 7 Drawing Sheets

(56) References Cited

U.S. PATENT DOCUMENTS

| | | | |
|---|---|---|---|
| 2003/0060831 A1 | 3/2003 | Bonutti | |
| 2007/0167709 A1* | 7/2007 | Slayton | A61B 8/463 |
| | | | 600/407 |
| 2009/0306509 A1* | 12/2009 | Pedersen | A61B 8/4254 |
| | | | 600/446 |
| 2011/0282200 A1 | 11/2011 | Yen et al. | |
| 2011/0313293 A1* | 12/2011 | Lindekugel | A61B 8/44 |
| | | | 600/461 |
| 2014/0257104 A1 | 9/2014 | Dunbar et al. | |
| 2015/0080710 A1* | 3/2015 | Henkel | A61B 8/14 |
| | | | 600/424 |
| 2015/0148664 A1 | 5/2015 | Stolka et al. | |
| 2015/0150464 A1* | 6/2015 | Boctor | A61B 5/0084 |
| | | | 600/424 |
| 2016/0314715 A1* | 10/2016 | Savitsky | G09B 23/286 |
| 2016/0331269 A1 | 11/2016 | Kruger et al. | |
| 2019/0231387 A1* | 8/2019 | Allaway | A61B 8/0841 |

FOREIGN PATENT DOCUMENTS

| | | | |
|---|---|---|---|
| JP | 2008-284144 A | | 8/2013 |
| KR | 2009124310 A | * | 12/2009 |
| KR | 20090124310 A | | 12/2009 |
| KR | 1020090124310 A | | 12/2009 |
| WO | 2007/040172 A1 | | 4/2007 |
| WO | 2015039302 A1 | | 3/2015 |
| WO | 2015159129 A1 | | 10/2015 |

OTHER PUBLICATIONS

Franz et al., Combined Modality for Ultrasound Imaging and Electromagnetic Tracking, Biomedizinische Technik/Biomedical Engineering, Sep. 2013, vol. 58, 2 pages.

März et al., Interventional real-time ultrasound imaging with an integrated electromagnetic field generator, International Journal of Computer Assisted Radiology and Surgery, Mar. 25, 2014, vol. 9, 136 pages.

Franz, Workflow-Integrated Electromagnetic Tracking for Navigated Ultrasound-Guided Interventions, Deutschen Krebsforschungszentrum Heidelberg, Jan. 2015, 244 pages.

Winterstein, Ein ultraschallbasiertes Computerassistenzsystem mit integriertem elektromagnetischem Feldgenerator für die Leberchirurgie, 15 master thesis, Apr. 2014, Darmstadt University of Applied Sciences, 126 pages.

März, Computer-assistierte Punktionen unter Ultraschallfuhrung mit einem mobilen elektromagnetischen Feldgenerator, master thesis, Jan. 2013, Heidelberg University and Heilbronn University, 105 pages.

International Search Report; European Patent Office; International Application No. PCT/EP2018/059886; dated Jul. 12, 2018; 4 pages.

Written Opinion of the International Searching Authority; European Patent Office; International Application No. PCT/EP2018/059886; dated Jul. 12, 2018; 7 pages.

Final Office Action; Japanese Patent Office; Japanese Application No. 2019-556857; dated Sep. 13, 2022; 9 pages.

* cited by examiner

MOUNTING DEVICE FOR REVERSIBLY MOUNTING AN ELECTROMAGNETIC FIELD GENERATOR ON AN ULTRASONIC PROBE

CROSS-REFERENCE TO RELATED APPLICATIONS

This application is a U.S. National Phase of International PCT Application No. PCT/EP2018/059886 filed on Apr. 18, 2018, which claims the benefit of European Patent Application Serial No. 17167015.1 filed on Apr. 19, 2017, the contents of each of which are incorporated herein by reference in their entirety.

FIELD OF THE INVENTION

The invention relates to a mounting device for reversibly mounting at least one electromagnetic field generator on an ultrasonic probe, a mounting system, a mounting assembly and an ultrasonic probe, each at least partially comprising the mounting device.

RELATED ART

Sonography generally refers to an application of ultrasound to image parts of the human or animal body. Ultrasonic probes are commonly used, especially in medical diagnostics of humans and animals, for a creation of two-dimensional or three-dimensional images, in particular of body parts or tissues of the human or animal. Thus, sonography may be applied in order to visualize and evaluate a condition of a tissue, such as a presence of a tumor, injuries or physical lesions, in order to detect a pregnancy or in prenatal care. Sonography can further be applied as a modality in order to guide an instrument placement during an intervention, in particular, a minimally invasive procedure, such as a needle biopsy. Continuous localization of the instrument relative to the anatomy localized in the ultrasonic image, which is usually referred to as "tracking", can be facilitated by an application of an electromagnetic field generated by an electromagnetic field generator.

U.S. Pat. No. 7,926,776 B2 discloses a bracket for mounting at least one position detecting sensor on an ultrasonic probe. Herein, the bracket is used to releasably mount at least one 3D tracking sensor on an ultrasound transducer. In US 2015/0148664 A1 an ultrasound system with stereo image guidance or tracking is disclosed. The image-guided ultrasound system comprises an ultrasonic probe, a display configured to communicate with the ultrasonic probe to receive ultrasound signals to display images from the ultrasonic probe, and an imaging device. The imaging device is at least one of removably attached to or integral with the ultrasonic probe. Further, WO 2015/159129 A1 describes an instrument guide for a probe head of an ultrasound imaging probe. The instrument guide comprises a probe support region, a first guide bracket, a second guide bracket, a first guide disposed in the first guide bracket and a second guide disposed in the second guide bracket. Furthermore, US 2011/0313293 A1 discloses a cap for use with an ultrasonic probe. The probe cap comprises a body defining a cavity into which a head portion of the probe is removably received. The cap further comprises stabilization arm extending from the cap body for stabilizing the cap against a skin surface of a patient. Furthermore, the cap comprises a needle guide included with the cap.

Franz et al., *Combined modality for ultrasound imaging and electromagnetic tracking*. Biomed Tech 2013; 58 (Suppl. 1), März et al., *Interventional real-time ultrasound imaging with an integrated electromagnetic field generator*, Int J CARS 2014; 9(5) pp 759, and März et al., *Mobile EM Field Generator for Ultrasound Guided Navigated Needle Insertions*, LNCS 7915 Information Processing in Computer-Assisted Interventions, Jun. 26, 2013, pp 71, describe a combined modality comprising an ultrasonic probe and a compact electromagnetic field generator, wherein the compact electromagnetic field generator is mounted on the ultrasonic probe. The combined modality shows robust ultrasound imaging and electromagnetic tracking. In Adrian Winterstein, *Ein ultraschallbasiertes Compuleras-sistenzsystem mit integriertem elektromagnetischem Feldgenerator für die Leberchirurgie*, master thesis. April 2014, Darmstadt University of Applied Sciences, Keno März, *Computerassistierte Punktionen unter Ultraschallführung mit einem mobilen elektromagnetischen Feldgenerator*, master thesis. January 2013. Heidelberg University and Heilbronn University, and Alfred Franz, *Workflow-integrated Electromagnetic Tracking for Navigated Ultrasound-guided Interventions*, dissertation, October 2015. Heidelberg University, a combined modality comprising an ultrasonic probe and a compact electromagnetic field generator is disclosed, wherein the compact electromagnetic field generator is mounted on the ultrasonic probe in a manner that a ring-like structure of the electromagnetic field generator surrounds a section of the ultrasonic probe.

Further. US 2011/282200 A1 describes a handheld accessory system for an ultrasonic equipment and an inspection method applicable to the accessory system. The accessory system includes a force detector and a positioning device attached to a hand-held ultrasonic probe, and a signal processing device. A user may apply the ultrasonic probe to the target tumor with a certain compression depth. A force compensation module in the signal processing device allows to make compensation due to unsteady compression depth, thereby providing for the operation of transverse palpation to detect the stiffness ratio and mobility of a target relative to its surrounding tissues, and being therefore specifically suitable for diagnosing breast tumors, as benign or malignant.

Furthermore, US 2014/257104 A1 discloses a system and method for assembling a 3D ultrasound image representation from multiple two-dimensional ultrasound images utilising a magnetic position detection system to detect the ultrasound probe position and allow mapping of the multiple two-dimensional ultrasound images into a three-dimensional frame of reference. The magnetic position detection system may use magnetic markers positioned on the subject or fixed in space around the subject. The position detection may use magnetic model fitting, look-up table, triangulation or distance measurement techniques to determine the position of the ultrasound probe relative to the magnetic markers. The ultrasound probe includes a magnetometric detector to detect the field generated by the magnetic markers.

Moreover. KR 2009 0124310 A relates to an ultrasonic probe configured for being connected to an attachment device.

Despite the recent advances concerning devices for mounting an electromagnetic field generator onto an ultrasonic probe, there is still room for improvement.

Problem to be Solved

It is therefore an objective of the present invention to at least partially overcome deficiencies of state of the art. In particular, many mounting devices may, as a general rule, be combinable with only a subset of ultrasonic probes, such as with one particular ultrasonic probe, for example with the ultrasonic probe of a certain supplier. Further, mounting devices may in general be configured to mount an electromagnetic field generator in just a single or a limited number of mounting positions on an ultrasonic probe. This lack of flexibility in mounting the electromagnetic field generator on the ultrasonic probe may, in general, be a disadvantage, especially in clinical practice where a user may intend to orientate the ultrasonic probe with respect to a patient, which may be desirable to be overcome.

SUMMARY OF THE INVENTION

This problem is solved by a mounting device for reversibly mounting at least one electromagnetic field generator, a mounting system, a mounting assembly and an ultrasonic probe having the features of the independent claims. Preferred embodiments of the invention, which may be realized in an isolated way or in any arbitrary combination, are disclosed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably". "particularly", "more particularly", "specifically", "more specifically" or similar terms are used in con-junction with optional features, without restricting alternative possibilities. Thus, features introduced by these terms are optional features and are not intended to restrict the scope of the claims in any way. The invention may, as the skilled person will recognize, be per-formed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a mounting device for mounting at least one electromagnetic field generator onto an ultrasonic probe for orientating the electromagnetic field generator with respect to the ultrasonic probe in at least one mounting position is disclosed. The mounting device comprises at least one first fastening structure. The mounting device is connectable to the electromagnetic field generator via the first fastening structure.

As used herein, the term "mounting device" may generally refer to an arbitrary device configured for bringing an object into a position or keeping an object in a position. As used herein, the term "reversibly mount" may generally refer to an arbitrary situation in which an object may be mounted and after having been mounted may be released or removed from the position in which it was mounted without being damaged. It is possible, that the object after having been removed from the position in which it was mounted may again be mounted in the same and/or in a different position. As used herein, the term "electromagnetic field generator" may generally refer to an arbitrary component configured to produce an electric and/or magnetic field. Additionally, the electromagnetic field generator may comprise a sensor array. As used herein, the term "sensor array" may generally refer to a device configured to receive an electric and/or magnetic signal. The electric and/or magnetic signal may in particular be emitted by an object to be localized by the sensor array or with the aid of the sensor array. Specifically, the electric and/or magnetic signal emitted by the object may contain information such as but not limited to a position of the object or an orientation of the object. As used herein, the term "ultrasonic probe" may generally refer to a component configured to transmit and/or receive ultrasound. An ultrasonic probe may also be referred to as an ultrasonic transducer. The ultrasonic probe may be configured to produce ultrasound, e.g. by converting electrical signals into ultrasound, or to convert ultrasound in electrical signals or both. Typically, ultrasonic probes, specifically ultrasonic probes used in medical diagnosis, may be classified as linear probes, sector probes and curved probes. The ultrasonic probe may further be combined or integrated with a light source, preferably a pulsed laser, configured to generate an optical signal, such as an electromagnetic wave in the optical spectrum, that may be converted into an acoustic signal, specifically an ultrasound signal, taking advantage of a photoacoustic effect. The ultrasonic probe may, in particular, be configured to receive the acoustic signal generated by the optical signal. A conversion from the optical to the acoustic signal taking advantage of the photoacoustic effect may, in particular, take place in the tissue of a patient. Thus, by receiving the acoustic signal the ultrasonic probe may be configured to measure additional properties of the tissue, typically optical or functional properties. As used herein, the terms "orient" or "orientate" may generally refer to locating a first object relative to a position, preferably, to at least one second object. In particular, the first object may be aligned with the second object. As used herein, the term "mounting position" may generally refer to an arbitrary position into which an object may be brought or in which an object may be held in order to achieve a mounting of the object. As used herein, the term "fastening structure" may generally refer to an arbitrary element configured to fix or to partake in fixing an object in a certain position or to connect or to partake in connecting the object to another object. The fastening structure may achieve fixing an object in a certain position or connecting an object to another object on its own, e.g. as a clip, and/or in cooperation and/or inter-action with another device or structure, e.g. another fastening structure. As used herein, the term "connectable" may generally refer to the property of an object that may be brought into and fixed in close physical proximity to another object. In particular, the object that is connectable to another object may be in direct or indirect physical contact with the other object when it is connected to it.

The mounting position may be a predefined mounting position. As used herein, the term "predefined mounting position" may generally refer to a mounting position that had been chosen and/or determined as a possible mounting position before the object was actually mounted. The predefined mounting position may be marked and/or identified as such, e.g. by optical marks, such as lines or dots, and/or physically, e.g. by one or more of a protrusion, an elevation, an indentation and a depression. Specifically, the predefined mounting position may facilitate a mounting of an object, e.g. by identifying a location, in which the object may be mounted rapidly and/or easily and/or in which the object, when mounted, is particularly stable. In a particular embodiment, the electromagnetic field generator may be mountable on the ultrasonic probe in at least two mounting positions by the mounting device. Specifically, the two mounting positions may be predefined mounting positions. Specifically, the two mounting positions may be located at two distinct sides of the ultrasonic probe. The two distinct sides may be essentially perpendicular to one another. Thus, the mounting device may provide at least two distinct mounting positions such that the electromagnetic field generator may be mounted onto the ultrasonic probe, unmounted from the ultrasonic probe and remounted at at least one different position without disconnecting the mounting device from the ultrasonic probe. This may be particularly advantageous for orienting the electromagnetic field generator with respect to the ultrasonic probe and, thus, for allowing to achieve a placement most ergonomic for the user during a clinical application.

In a particularly preferred embodiment, the mounting device may be arranged, preferably connectable to the ultrasonic probe, within an envelope of 5 cm of the ultrasonic probe. Further, the electromagnetic field generator may be attachable within an envelope of 5 cm of the ultrasonic probe when mounted on the ultrasonic probe by the mounting device. In other words, the electromagnetic field generator may be connectable to the ultrasonic probe within an envelope of 5 cm of the ultrasonic probe when mounted on the ultrasonic probe by the mounting device. As used herein, the term "envelope" may generally refer to a three-dimensional structure encompassing an object. The distance between a surface of the object and a surface of the envelope may have a constant value. Herein, the surface of the object and the surface of the envelope may be considered to assume the shortest distance. Thus, the envelope may have a three-dimensional shape that largely corresponds to a scaled-up three-dimensional shape of the ultrasonic probe. A distance between a surface of the envelope and a surface of the ultrasonic probe may have a constant value, in particular a constant value of 5 cm. When mounted on the ultrasonic probe by the mounting device, the electromagnetic field generator at its point most remote from the ultrasonic probe may have a distance to the ultrasonic probe of 5 cm or smaller. In particular, the distance between the electromagnetic field generator, at its point most remote from the ultrasonic probe, and the ultrasonic probe may be 1 cm to 5 cm. Thus, in particular, both the mounting device and the electromagnetic field generator may be arranged or may be arrangeable within an envelope of 5 cm of the ultrasonic probe when the electromagnetic field generator is connected to the ultrasonic probe by the mounting device. As used herein, a "distance" between two points or between a point and an object may generally refer to the shortest possible geometric trace between the two points or between the point and the object. In another particularly preferred embodiment, the electromagnetic field generator may be attachable within an envelope of 1 cm to 2 cm of the ultrasonic probe when mounted on the ultrasonic probe by the mounting device.

In a particularly preferred embodiment, the mounting device may be reversibly connectable to the ultrasonic probe. Specifically, the mounting device may be released or removed from the ultrasonic probe without being damaged after having been connected to the ultrasonic probe. In particular, the mounting device may subsequently again be connectable to the ultrasonic probe. Further, the mounting device may at least partially encompass the ultrasonic probe. As used herein, the term "at least partially encompass" may generally refer to the situation in which one object A encloses the circumference of another object B at least one position or section of the object B. Furthermore, the mounting device may at least partially encompass the electromagnetic field generator. In a preferred embodiment, the mounting device, in particular the first fastening structure, may comprise a strap or a sling. The strap or the sling may at least partially encompass the electromagnetic field generator.

Further, the mounting device may be formed by a single piece. As used herein the term "by a single piece" may generally refer to an element consisting of one component only or to an element consisting of at least two components which may be connected such that a disruption of the connection damages and/or destroys the element and/or renders the element unserviceable. Alternatively, the mounting device may comprise at least two components.

The mounting device comprises the first fastening structure. The first fastening structure may comprise at least one first fastening component configured to interact with a second fastening component. As used herein, the term "fastening component" may generally refer to an element configured to interact with another element, e.g. another fastening component, in order to form a connection between the two elements. Specifically, the connection may be reversible. Further, the first fastening component may comprise at least one of at least one element selected from the group consisting of: a male part of a press fastener; a female part of a press fastener, a male part of a press button; a female part of a press button; a protrusion; an indentation; an elevation; a depression; a plug connector; a plug socket; a pin; a pinhole; a button; a button hole; a hook of a hook-and-loop fastener; a loop of a hook- and loop fastener; a clip; a guide rail; a sliding fastener a snap-fit fastener; a pin fastener; a clutch; a clamp.

In a particularly preferred embodiment, the mounting device may further comprise at least one second fastening structure, wherein the mounting device may be connectable to the ultrasonic probe via the second fastening structure. The second fastening structure may comprise at least one element selected from the group consisting of: a bracket, a belt; a ring; a tie; a male part of a press fastener; a female part of a press fastener a male part of a press button; a female part of a press button; a protrusion; an indentation; an elevation; a depression; a plug connector, a plug socket; a pin; a pinhole; a button; a button hole; a hook of a hook-and-loop fastener; a loop of a hook- and loop fastener; a clip; a guide rail; a sliding fastener; a snap-fit fastener; a pin fastener, a clutch; a clamp. In a preferred embodiment, the second fastening structure may be formed by a single piece. In another preferred embodiment, the second fastening component may comprise at least two components. Specifically, the second fastening structure may comprise at least one first connection element and at least one second connection element. Herein, the mounting device may, preferably, be connectable to the ultrasonic probe via the first connection element while the second connection element may, preferably, be connectable to both the first connection element and the first fastening structure. As used herein, the term "connection element" may generally refer to a component configured to partake in connecting at least two objects A and B. When connected the two objects A and B may not be connected to one another directly and/or may not be in direct physical contact with one another. Instead, the two objects may be connected via at least one connection element and/or the two objects may each be in direct physical contact with the connection element, wherein the connection element the object A is connected to may differ from the connection element object B is connected to. Specifically, the connection element may partake in connecting at least two objects A and B by being itself connected to at least two components of the connection, such as but not limited to, to both objects A and B or to two connection elements or to one object A or B and one connection element or to one connection element and one fastening structure. The first connection element may comprise at least one element selected from the group consisting of: a bracket; a belt; a ring; a tie; a clip. The first connection element, in particular the bracket, the belt, the ring, and/or the tie, may be at least partially elastic or expandable and/or may comprise at least one elastic or expendable section. Further, the first connection element, in particular the bracket, the belt, the ring, and/or the tie, may be discontinuous, comprising at least two connectable elements, which in their entirety form the first connection element. As a particularly preferred example, the first connection element may be a bracket, preferably a bracket comprising a plastic material and/or a metal. The bracket may be openable and closable via at least one hinge. The bracket may form a ring-like structure in its closed state. Further, the bracket may be lockable in its closed state, e.g. by at least one screw and at least one screw-nut. Other mechanisms to lock the bracket in its closed state are feasible.

The second connection element may comprise the at least one second fastening component. Specifically, the second fastening component may comprise at least one of at least one element selected from the group consisting of: a male part of a press fastener; a female part of a press fastener a male part of a press button; a female pan of a press button; a protrusion; an indentation; an elevation; a depression; a plug connector a plug socket; a pin; a pinhole; a button; a button hole; a hook of a hook-and-loop fastener; a loop of a hook- and loop fastener; a clip; a guide rail; a sliding fastener; a snap-fit fastener, a pin fastener, a clutch; a clamp.

The first fastening structure and the second fastening structure may be connectable via at least one connection, specifically via at least one connection selected from the group consisting of: a snap-fit connection; a press button connection; a sliding connection; a clamp connection; a press-fastener connection; a button connection; a hook-and-loop connection; a pin connection; a clip connection; a clutch connection. In particular, the first fastening structure and the second fastening structure may be connectable via the first fastening component and the second fastening component.

The mounting device may be connectable to the ultrasonic probe in at least one connection position. In particular, the connection position may be a predefined connection position. As used herein, the term "connection position" may generally refer to an arbitrary position in which an object may be arranged when connected to a further object. Specifically, the at least one connection position may be located at at least one of: a base of the ultrasonic probe; and a neck of the ultrasonic probe; a base-neck-transition of the ultrasonic probe. As used herein, the term "base of an ultrasonic probe" may generally refer to a section of the ultrasonic probe that is closest to a patient or an element, when the patient or object is examined using the ultrasonic probe. As used herein, the term "neck of an ultrasonic probe" may generally refer to a further section of the ultrasonic probe which is attached to the base of the ultrasonic probe. The section that is referred to as "neck of the ultrasonic probe" may usually be used for handling purposes. Further, this section may usually have a slimmer shape compared to the base of the ultrasonic probe, e.g. the neck of the ultrasonic probe may have a smaller circumference than the ultrasonic probe. As used herein, the term "a base-neck-transition" may generally refer to a portion of the ultrasonic probe located between the base of the ultrasonic probe and the neck of the ultrasonic probe. In particular, a circumference of the ultrasonic probe may be altering within the base-neck-transition of the ultrasonic probe, e.g. from the larger circumference of the base of the ultrasonic probe to the smaller circumference of the neck of the ultrasonic probe.

The mounting device, in particular the second fastening structure, preferably the first connection element, most preferably the bracket, may comprise an extension arm. The extension arm may point along the ultrasonic probe towards a cable of the ultrasonic probe. The extension arm may have a length of 1 cm to 20 cm, preferably of 2 to 15 cm, more preferably of 3 to 10 cm. The extension arm may comprise the at least one mounting position. Thus, in a particularly preferred embodiment, the mounting device, in particular the first connection element may be connectable to the base, the base-neck transition or, preferably, the neck of the ultrasonic probe while the electromagnetic field generator may be mountable on the ultrasonic probe in a mounting position located alongside the cable of the ultrasonic probe. Orientating the electromagnetic field generator with respect to the ultrasonic probe in this mounting position may be particularly advantageous in interventions where the object to be localized is mainly to be found in an area around the neck of the ultrasonic probe, e.g. when a long instrument used for the intervention can only be tracked at its base or handle. This may ensure that the localized object may be positionable close to the field generator and, thus, always in the area of highest tracking accuracy.

The mounting device may be at least partially covered by a layer of anti-slip material. In particular, the layer of anti-slip material may face the ultrasonic probe when the electromagnetic field generator may be mounted on the ultrasonic probe via the mounting device. Specifically, the anti-slip material may be minimally compressible. In a preferred embodiment the anti-slip material may comprise at least one material selected from the group consisting of: a gecko tape; a grip tape; a non-slip foam. In particular, the second fastening structure may be at least partially covered with the layer of anti-slip material. More particularly, the first connection element may be at least partially covered with the layer of anti-slip material. For example, the bracket may be at least partially covered with the layer of anti-slip material.

The mounting device, in particular the first fastening structure, may be reversibly connectable to the electromagnetic field generator. In a preferred embodiment, the first fastening structure may be a strap configured to reversibly receive the electromagnetic field generator. Alternatively, a connection between the mounting device, in particular the first fastening structure, and the electromagnetic field generator may be irreversible. As used herein, the term "irreversible connection" may generally refer to a connection of two objects, wherein the two objects may not be detachable when connected. Additionally or alternatively, a detachment of the two objects may render at least one of the two objects unserviceable.

The electromagnetic field generator may be firmly adhered to the mounting device. Specifically, the electromagnetic field generator may be firmly adhered to the first fastening structure. As used herein, the term "firmly adhered to" may generally refer to an object being stably connected to another object, for example via glue and/or an adhesive and/or an adhesive strip. The two objects may be detachable from one another, for example by means of an aid such as but not limited to a solvent. A detachment of the mounting device, in particular of the first fastening structure, from the electromagnetic field generator may render the mounting device, in particular the first fastening structure, unserviceable. Alternatively, the mounting device, in particular the first fastening structure, may be reusable, for example by equipping the mounting device, particularly the first fastening structure with a new adhesive strip.

Further, the ultrasonic probe may be firmly adhered to the mounting device, Specifically, the ultrasonic probe may be firmly adhered to the second fastening structure. A detachment of the mounting device, in particular of the second fastening structure, from the ultrasonic probe may render the mounting device, in particular the second fastening structure, unserviceable. Alternatively, the mounting device, in particular the second fastening structure, may be reusable, for example by equipping the mounting device, particularly the second fastening structure with a new adhesive strip.

The mounting device may be combinable with an attachable instrument, in particular, with a needle guide. As used herein, the term "combinable" may generally refer two objects being usable simultaneously. In particular, the needle guide may be connectable to the ultrasonic probe when the electromagnetic field generator is mounted on the ultrasonic probe via the mounting device. Alternatively or in addition, the mounting device may be combinable with other attachable instruments, such as but not limited to a sensor holder for electromagnetic or other sensors, a projector to project image or other information onto the patient, a light or laser source to emit a light signal into the tissue. In particular, the attachable instrument, especially, the needle guide, may be combinable with the mounting device by using a separate device for attaching the attachable instrument. Alternatively or in addition, the mounting device may comprise a further attachment element adapted for mounting the attachable instrument on the ultrasonic probe using the mounting device. Thus, the mounting device may be configured to mount the at least one electromagnetic field generator and the at least one attachable instrument, in particular the needle guide, on the ultrasonic probe simultaneously. Further, the mounting device may be connectable to a variety of ultrasonic probes. In particular, the mounting device may be connectable to at least two different ultrasonic probes. Further, the mounting device may be at least partially integrated into a housing of the ultrasonic probe. In particular, the second fastening structure may be at least partially integrated into the housing of the ultrasonic probe. Specifically, the first connection element and/or the second connection element may be at least partially integrated into the housing of the ultrasonic probe.

In a particularly preferred embodiment, the mounting device may comprise at least two, preferably three, connectable parts, which when connected may reproduce the three-dimensional shape of the ultrasonic probe at least to a large extent. This may be particularly advantageous for providing an ergonomic shape of the mounting device and/or for providing a high stability of the connection between the mounting device and the ultrasonic probe and/or between the electromagnetic field generator and the ultrasonic probe. Specifically, the connectable parts may cover the ultrasonic probe except for functional elements that require direct accessibility. In particular, the at least two parts may be formed using a cast of the ultrasonic probe or a part thereof. Specifically, the at least two, preferably three, parts may together form or may together comprise the second fastening structure. In particular, the connectable parts may be connectable via at least one snap-in mechanism. Other mechanisms are feasible.

The electromagnetic field generator may have no mechanical play with respect of the ultrasonic probe when the electromagnetic field generator is mounted on the ultrasonic probe via the mounting device.

In a further aspect, a mounting system is disclosed. The mounting system comprises a mounting device as described elsewhere in this document. The mounting system further comprises an electromagnetic field generator. Herein, the electromagnetic field generator is attached within an envelope of 5 cm of the ultrasonic probe when mounted on the ultrasonic probe by the mounting device. In particular, the electromagnetic field generator may have a dimension below 5 cm. As used herein, the term "dimension" may generally refer to an extension of the electromagnetic field generator. As a specific example, the dimension of the electromagnetic field generator may be an edge length or a diameter of the electromagnetic field generator, in particular, of a cuboid-shaped electromagnetic field generator. In particular, the cuboid-shaped electromagnetic field generator may have an edge length of below 5 cm, preferably below 2 cm, in particular below 1 cm. By way of example, the electromagnetic field generator may be cuboid-shaped having an edge length of 0.5 cm to 4.5 cm. In another particularly preferred embodiment, the electromagnetic field generator may have an edge length of 0.75 cm to 1.5, most preferably of 1 cm.

In a further aspect, a mounting assembly is disclosed. The mounting assembly comprises a mounting system as described elsewhere in this document. The mounting assembly further comprises an ultrasonic probe. In a preferred embodiment, a mounting device may be at least partially integrated into a housing of the ultrasonic probe. As used herein, the term "housing" may generally refer to a component of an object that confines the object against its surroundings. In a preferred embodiment, a second fastening structure may at least partially be integrated into the housing of the ultrasonic probe.

In a further aspect, an ultrasonic probe is disclosed. Herein, a mounting device as described elsewhere in this document is at least partially integrated into a housing of the ultrasonic probe. In a preferred embodiment, a second fastening structure may at least partially be integrated into the housing of the ultrasonic probe. In a further preferred embodiment, an electromagnetic field generator may be at least partially integrated into the housing of the ultrasonic probe.

In a further aspect, a use of a mounting device for orientating at least one electromagnetic field generator with respect to at least one element selected from the group consisting of a patient, a body part of the patient, a section of the body part of the patient, a tissue of the patient, a needle guide is disclosed. Thus, the mounting device may be used to mount the electromagnetic field generator onto an ultrasonic probe in a mounting position such that the mounted electromagnetic field generator allows or facilitates at least one of an examination, a treatment, or a medical intervention such as but not limited to a minimally invasive procedure, in particular a needle biopsy.

For further details regarding the mounting device, the mounting system, the mounting assembly, the ultrasonic probe, and the use of the mounting device, as well as definitions of terms used to further describe the mounting device, the mounting system, the mounting assembly, the ultrasonic probe, and the use of the mounting device reference may be made to the description of the mounting device elsewhere in this document.

SHORT DESCRIPTION OF THE FIGURES

Further Details of the invention may be derived from the following disclosure of preferred embodiments. The features of the embodiments may be realized in an isolated way or in any combination. The invention is not restricted to the embodiments. The embodiments are schematically depicted in the figures. Identical reference numbers in the figures refer to identical elements or functionally identical elements or elements corresponding to each other with regard to their functions.

These Figures and the various features comprised therein will be elucidated in a combined fashion below.

DETAILED DESCRIPTION OF THE EMBODIMENTS

Figure 1:
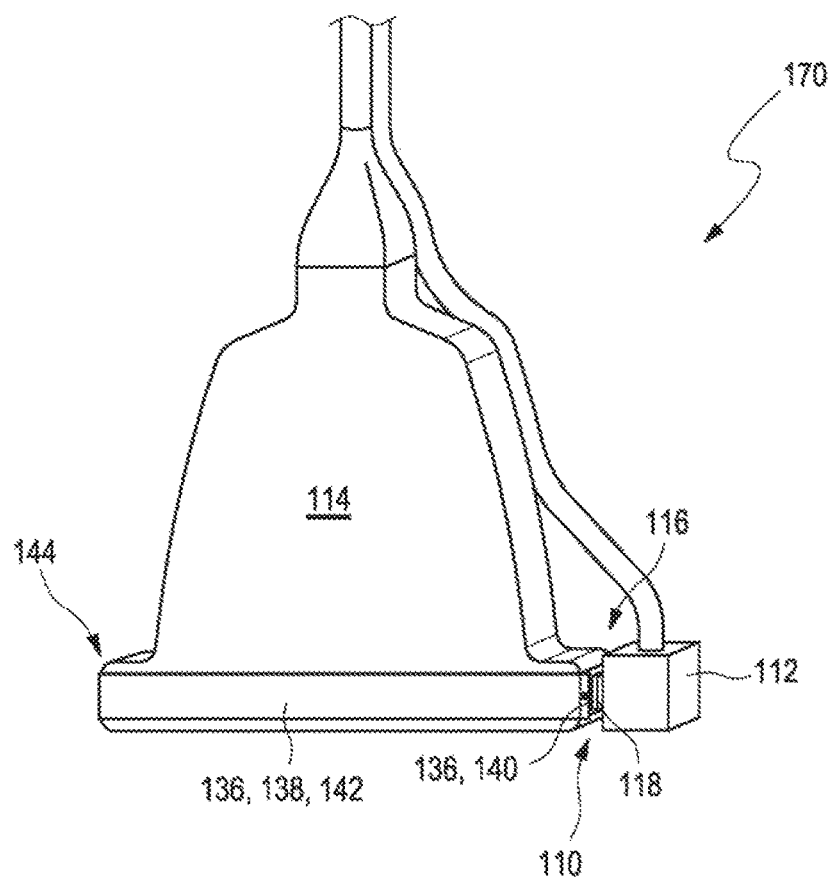
FIG. 1 shows an electromagnetic field generator mounted onto an ultrasonic probe via a mounting device.

FIG. 1 shows a mounting device 110 for reversibly mounting at least one electromagnetic field generator 112 on an ultrasonic probe 114 for orienting the electromagnetic field generator 112 with respect to the ultrasonic probe 114 in at least one mounting position 116. The mounting device 110 comprises at least one first fastening structure 118. The mounting device 110 is connectable to the electromagnetic field generator 112 via the first fastening structure 118. FIG. 1 further shows the electromagnetic field generator 112 mounted onto the ultrasonic probe 114 via the mounting device 110.

Figure 2:
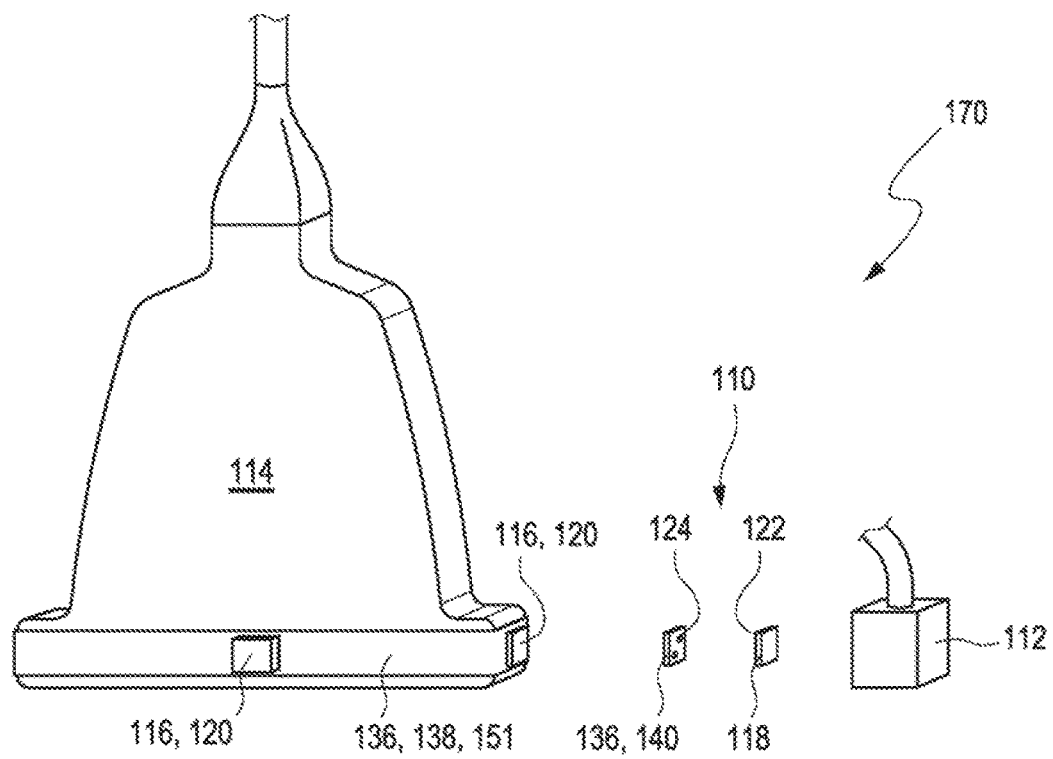
FIG. 2 shows an exploded view of a preferred embodiment of the mounting device together with the electromagnetic field generator and the ultrasonic probe.
Figure 4:
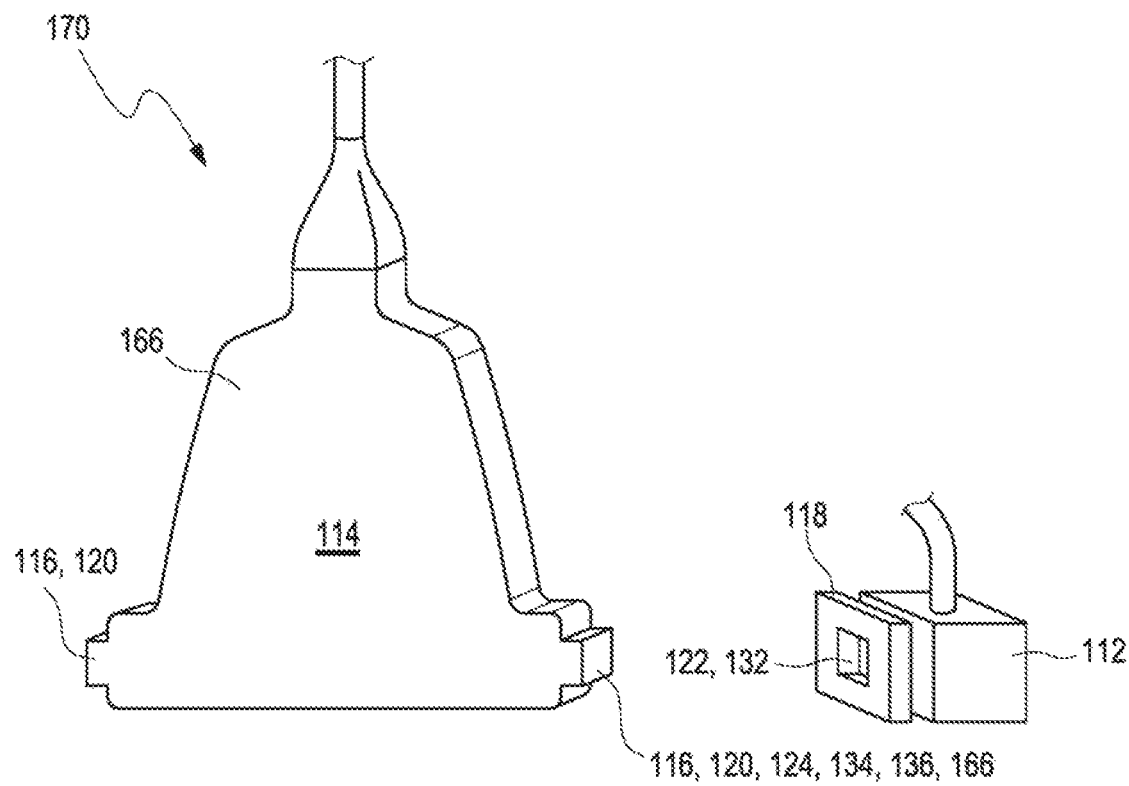
FIG. 4 shows another preferred embodiment of the mounting device together with an electromagnetic field generator and an ultrasonic probe.
Figure 5:
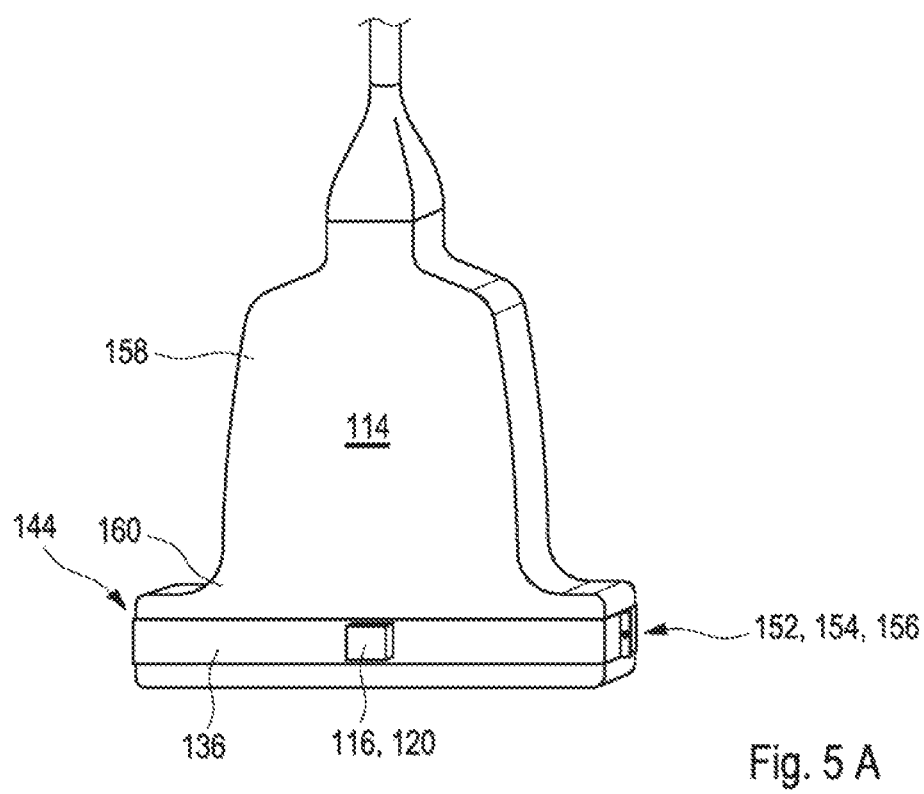
FIGS. 5A to 5C show different embodiments of a second fastening structure of the mounting device mounted in three different connection positions on a base of the ultrasonic probe (FIG. 5A), on a base-neck transition of the ultrasonic probe (FIG. 5B) and on a neck of the ultrasonic probe (FIG. 5C)
Figure 5:
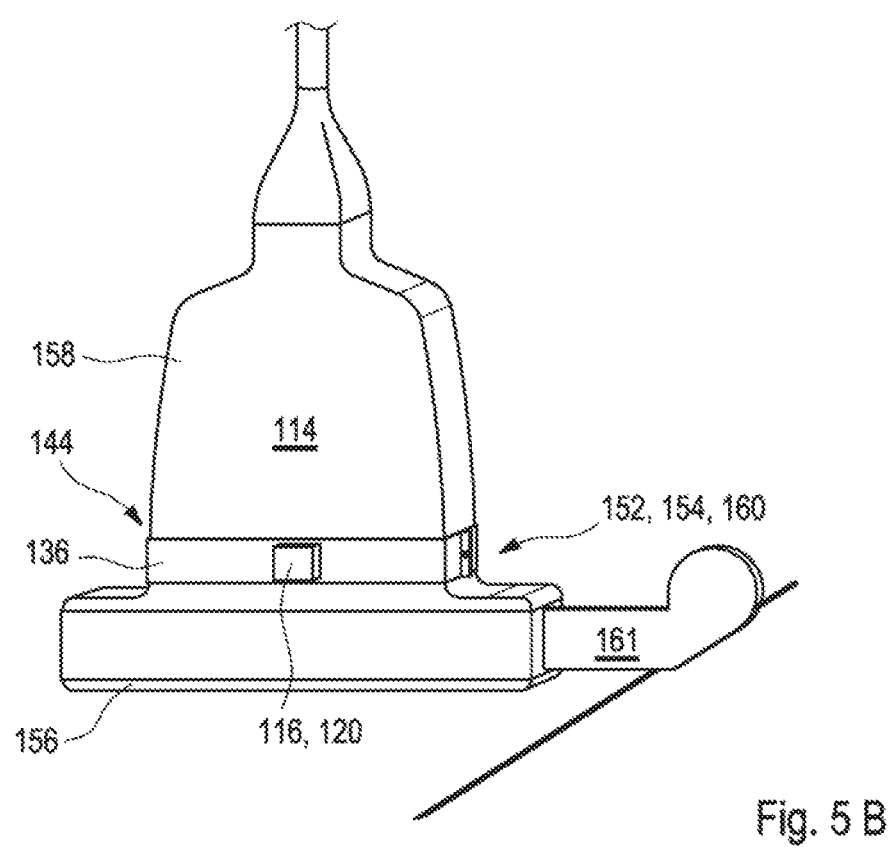
Figure 5:
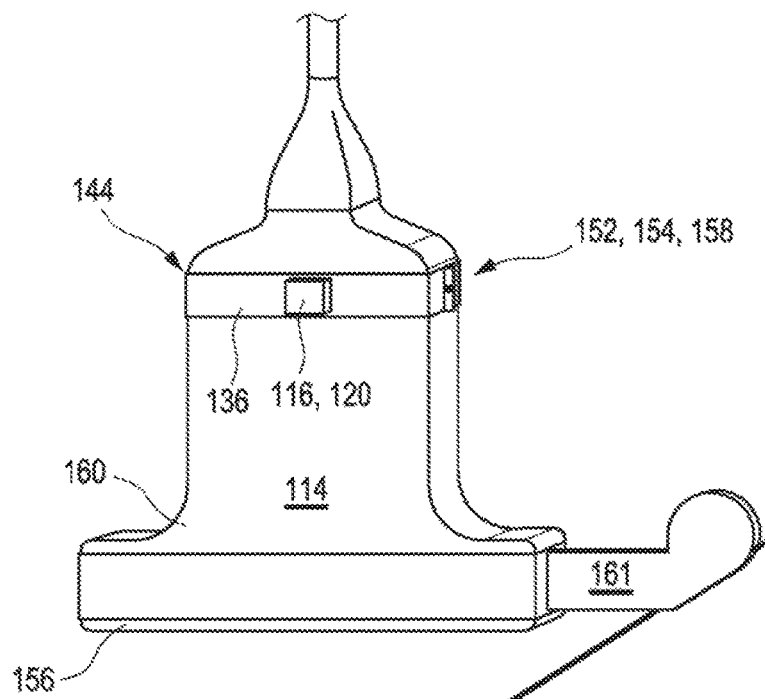
Figure 6:
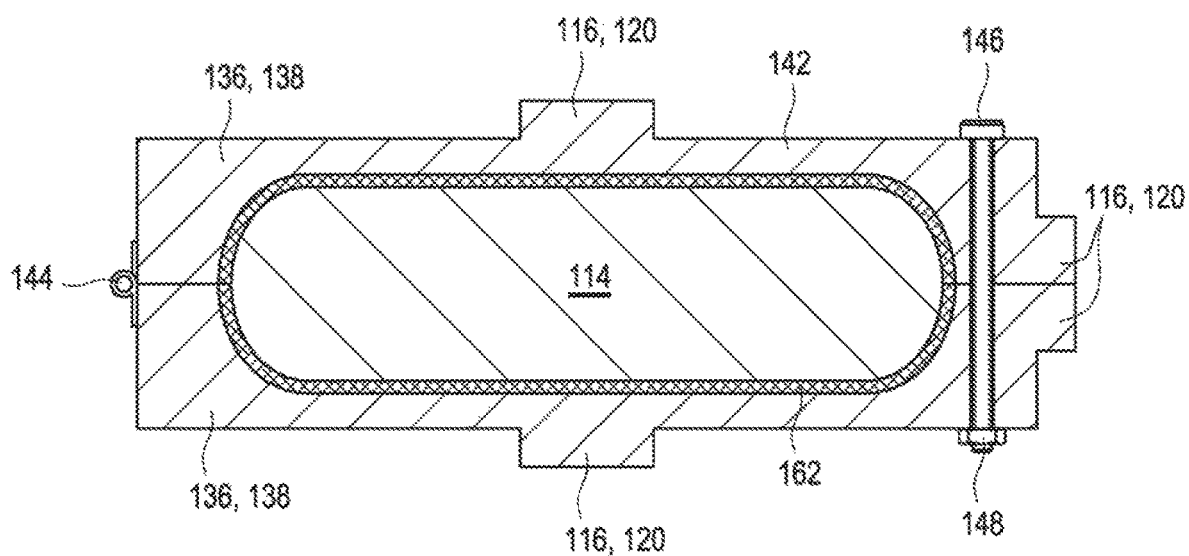
FIG. 6 shows a first connection element of the mounting device mounted onto the ultrasonic probe in a bottom view.

The electromagnetic field generator may be mounted in a predefined mounting position 120. The predefined mounting position 120 may be marked for example by a protrusion as can be seen in FIGS. 2, 4, 5A to 5C and in FIG. 6. However, the predefined mounting position 120 may also be marked by other means such as by optical marks such as lines or dots. As shown in FIGS. 2, 4 and 6 the mounting device 110 may comprise two or more mounting positions 116, in particular two or more predefined mounting positions 120 for mounting the electromagnetic field generator 112 on the ultrasonic probe 114. Thus, the mounting device 110 may provide at least two distinct mounting positions 120 such that the electromagnetic field generator 112 may be mounted onto the ultrasonic probe 114, unmounted from the ultrasonic probe 114 and remounted at at least one different mounting position 120 without disconnecting the mounting device 110 from the ultrasonic probe 114. Specifically, the at least two mounting positions 120 may be located at two distinct sides of the ultrasonic probe 114. The two distinct sides may be essentially perpendicular to one another, as e.g. illustrated in FIG. 2. The two distinct sides may, however, also confine a different angle or be parallel, as e.g. illustrated in FIGS. 4 and 6.

Figure 7A:
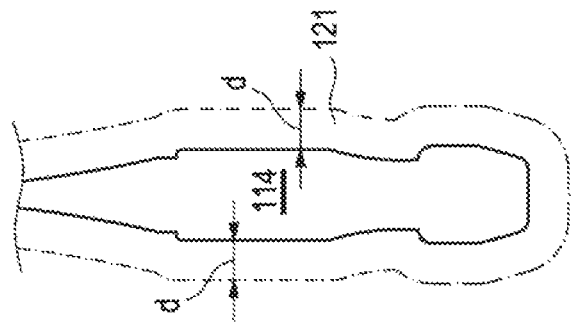
FIGS. 7A to 7C show an envelope of the ultrasonic probe in two side views (FIGS. 7A and 7C) and a bottom view (FIG. 7B)
Figure 7B:
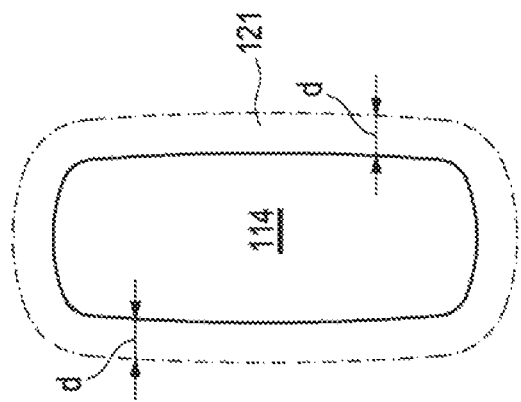
Figure 7C:
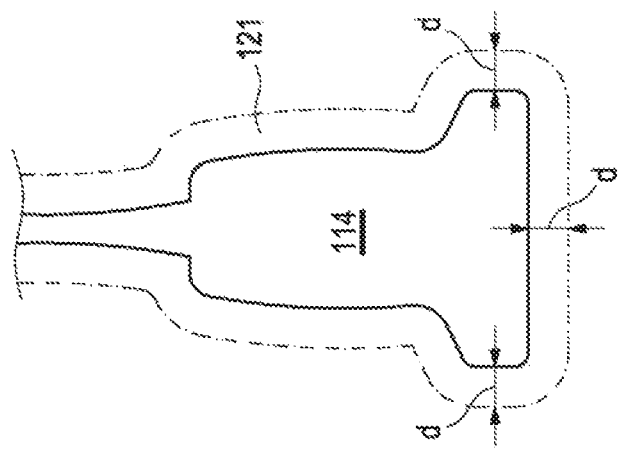

The electromagnetic field generator 112 may be attachable within an envelope 121 of 5 cm of the ultrasonic probe 114 when mounted on the ultrasonic probe 114 by the mounting device 110. In other words, the electromagnetic field generator 112 may be connectable to 23 the ultrasonic probe 114 within an envelope 121 of 5 cm of the ultrasonic probe 114 when mounted on the ultrasonic probe 114 by the mounting device 110. A distance d between a surface of the envelope 121 and a surface of the ultrasonic probe may have a constant value, such as illustrated in FIGS. 7A, 7B and 7C, in particular a constant value of 5 cm. Further, the mounting device 110 may be arranged, preferably connectable to the ultrasonic probe 114, within an envelope of 5 cm of the ultrasonic probe 114. Thus, in particular, both the mounting device 110 and the electromagnetic field generator 112 may be arranged or may be arrangeable within an envelope of 5 cm of the ultrasonic probe 114 when the electromagnetic field generator 112 is connected to the ultrasonic probe 112 by the mounting device 110. The envelope 121 of the ultrasonic probe 114 is shown in two side views in FIGS. 7A and 7C and a bottom view in FIG. 7B. As is apparent from a synopsis of FIGS. 7A, 7B and 7C, the envelope 121 may have a three-dimensional shape that largely corresponds to a scaled-up three-dimensional shape of the ultrasonic probe 114. When mounted on the ultrasonic probe 114 by the mounting device 110, the electromagnetic field generator 112 at its point most remote from the ultrasonic probe 114 may have a distance to the ultrasonic probe of 5 cm or smaller. In particular, the distance between the electromagnetic field generator 112 at its point most remote from the ultrasonic probe 114 and the ultrasonic probe 114 may be 1 cm to 5 cm.

Figure 3:
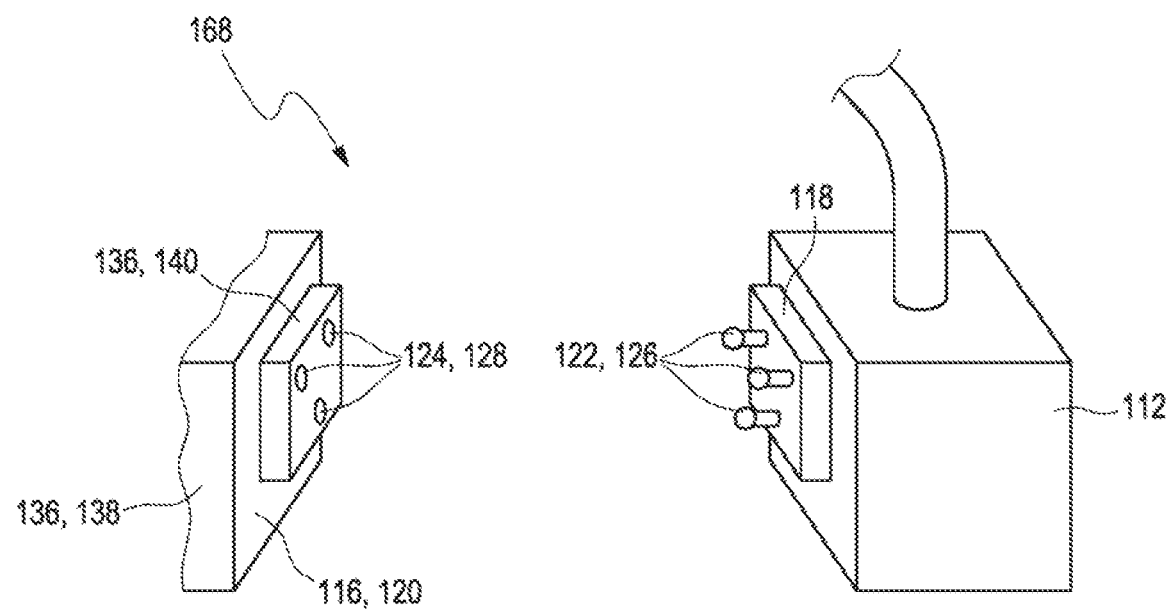
FIGS. 3A to 3C show each a partial view of a different embodiment of the mounting device and an electromagnetic field generator.
Figure 3:
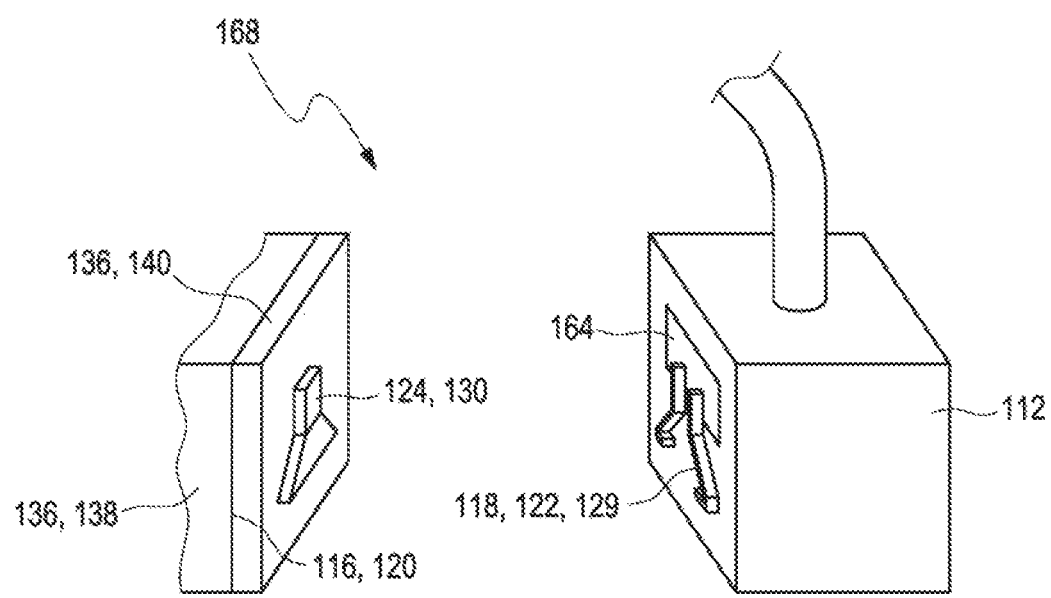
Figure 3:
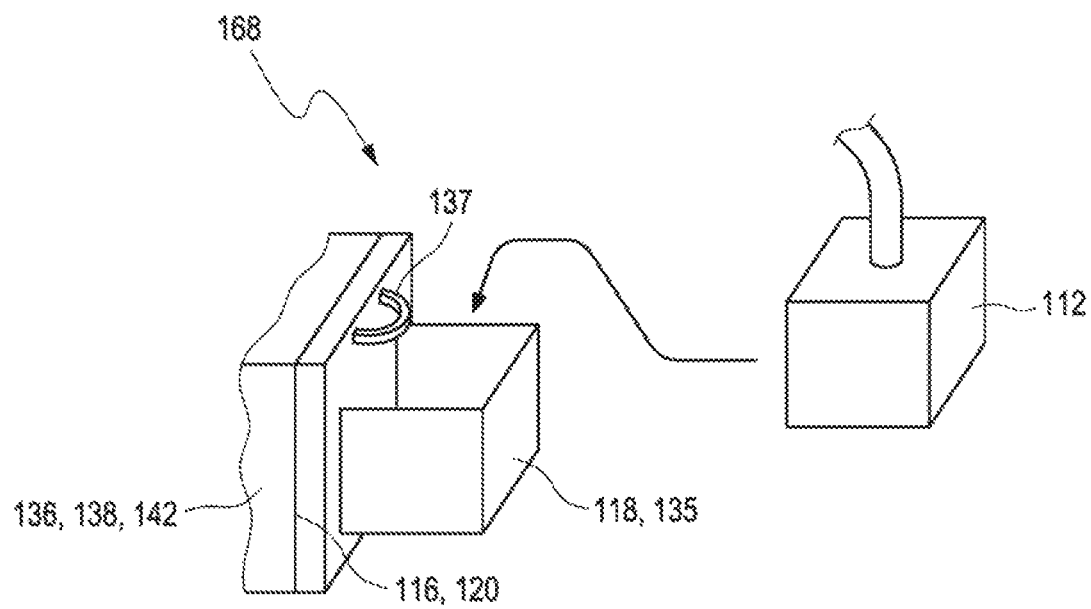

The mounting device 110 comprises the first fastening structure 118. The first fastening structure may comprise at least one first fastening component 122 configured to interact with a second fastening component 124. The first fastening component 122 and the second fastening component 124 may interact to form a connection that may be reversible. In a first embodiment, the first fastening component 122 may for example be a male part of press button 126 and the second fastening component 124 may be a female part of a press button 128 as shown in FIG. 3A. In an alternative embodiment, the first fastening component 122 may be a snap-fit fastener 129 and the second fastening component 124 may be a guide rail 130 as shown in FIG. 3B. In a further embodiment, the first fastening component 122 may be an indentation 132 and the second fastening 124 component may be a protrusion 134 as shown in FIG. 4. Specifically, the first fastening component 122 and the second fastening component 124 may be selected from the group consisting of: a male part of a press fastener; a female part of a press fastener; a male part of a press button (126); a female part of a press button (128); a protrusion (134); an indentation (132); an elevation; a depression; a plug connector, a plug socket; a pin; a pinhole; a button; a button hole; a hook of a hook-and-loop fastener; a loop of a hook- and loop fastener; a clip; a guide rail (130); a sliding fastener; a snap-fit fastener (129); a pin fastener; a clutch; a clamp. In another preferred embodiment shown in FIG. 3C, the first fastening structure 118 may comprise a strap 135. The strap 135 may at least partially encompass the electromagnetic field generator 112. Further, the strap 135 may be configured to reversibly receive the electromagnetic field generator 112. As also shown in FIG. 3C, the mounting device 110, in particular the first fastening structure 118, may comprise a cable guide 137.

The mounting device 110 may comprise a second fastening structure 136, wherein the mounting device 110 is connectable to the ultrasonic probe 114 via the second fastening structure 136. The second fastening structure 136 may be formed by a single piece. Alternatively, the second fastening structure 136 may comprise at least two components. Specifically, the second fastening structure 136 may comprise at least one first connection element 138 and at least one second connection element 140, the mounting device 110 being connectable to the ultrasonic probe 114 via the first connection element 138, the second connection element 140 being connectable to both the first connection element 138 and the first fastening structure 118. The first connection element 138 may be a bracket 142 as shown in FIGS. 1, 5A to 5C and 6. Specifically, the bracket 142 may comprise a plastic material and/or a metal. The bracket 142 may be openable and closable via at least one hinge 144 as shown in FIGS. 1, 5A to 5C and 6. Further, the bracket 142 may be lockable in its closed state, e.g. by a screw 146 and a screw-nut 148 as shown in FIG. 6. Alternatively, the first connection element 138 may be formed by a flexible material. In a preferred embodiment, the first connection element 138 may be a ring 151 comprising a flexible material as shown in FIG. 2. The ring 151 comprising a flexible material may be connectable to the ultrasonic probe 114 due to the flexibility of the flexible material, which may allow a bending of the ring 151 to enlarge its circumference to impose it on the ultrasonic probe 114. Once imposed on the ultrasonic probe 114, the ring 151 comprising a flexible material may reassume its original shape to establish a tight fit of the ring 151 around the ultrasonic probe 114. Other possibilities for the first connection element 138 such as but not limited to a belt, a tie and a clip are feasible. The first connection element 138, in particular the bracket 142, the belt, the ring and/or the tie may be at least partially elastic or expandable.

Specifically, the second connection element 140 may comprise the at least one second fastening component 124. The first fastening structure 118 and the second fastening structure 136 may be connectable via the first fastening component 122 and the second fastening component 124 as depicted in FIG. 2 and FIGS. 3A and 3B.

The mounting device 110 may be connectable to the ultrasonic probe 114 in at least one connection position 152. In particular, the connection position 152 may be a predefined connection position 154. FIGS. 5A to 5C show the mounting device 110 connected to the ultrasonic probe 114 in different connection positions 152. Specifically, the connection position 152 may be located at a base of the ultrasonic probe 156 as shown in FIG. 5A; a neck of the ultrasonic probe 158 as shown in FIG. 5C or a base-neck-transition of the ultrasonic probe 160 as shown in FIG. 58. Further, the mounting device 110 may be combinable with a needle guide 161 as depicted in FIGS. 5B and 5C. The mounting device 110 may also be combinable with other attachable instruments (not shown), such as but not limited to a sensor holder for electromagnetic or other sensors, a projector to project image or other information onto the patient. Alternatively or in addition, the mounting device 110 may comprise a further attachment element adapted for mounting the attachable instrument on the ultrasonic probe 114 using the mounting device 110. Thus, the mounting device 110 may be configured to mount the at least one electromagnetic field generator 112 and the at least one attachable instrument, in particular the needle guide 161, on the ultrasonic probe 114 simultaneously (not shown in the Figures).

The mounting device 110 may be at least partially covered by a layer of anti-slip material 162. In particular, the second fastening structure 136 may be at least partially covered with the layer of anti-slip material 162. More particularly, the first connection element 138 may be at least partially covered with the layer of anti-slip material 162. As shown in FIG. 6, the bracket 142 may be at least partially covered with the layer of anti-slip material 162, In particular, the layer of anti-slip material 162 may face the ultrasonic probe 114 when the bracket 142 is mounted on the ultrasonic probe 114. Furthermore, as an alternative or in addition to the anti-slip material (162) of the second fastening structure, a cast may be modeled from the shape of the ultrasonic probe ensuring a tight fit of the second fastening structure at the ultrasonic probe. The cast may, in particular, be made of a thermoplastic material, such as a polyurethane elastomer.

The electromagnetic field generator 112 may be firmly adhered to the mounting device 110. Specifically, the electromagnetic field generator 112 may be firmly adhered to the first fastening structure 118 as shown in FIGS. 3A and 3B. FIG. 3B shows the first fastening structure 118 being adhered to the electromagnetic field generator 112 via an adhesive strip 164. Further, the ultrasonic probe 114 may be firmly adhered to the mounting device 110. Specifically, the ultrasonic probe 114 may be firmly adhered to the second fastening structure 136.

Further, the mounting device 110 may be at least partially integrated into a housing of the ultrasonic probe 166. In particular, the second fastening structure 136 may be at least partially integrated into the housing 166 of the ultrasonic probe 114 as shown in FIG. 4. In a further preferred embodiment, an electromagnetic field generator may be at least partially integrated into the housing of the ultrasonic probe.

Figure 8:
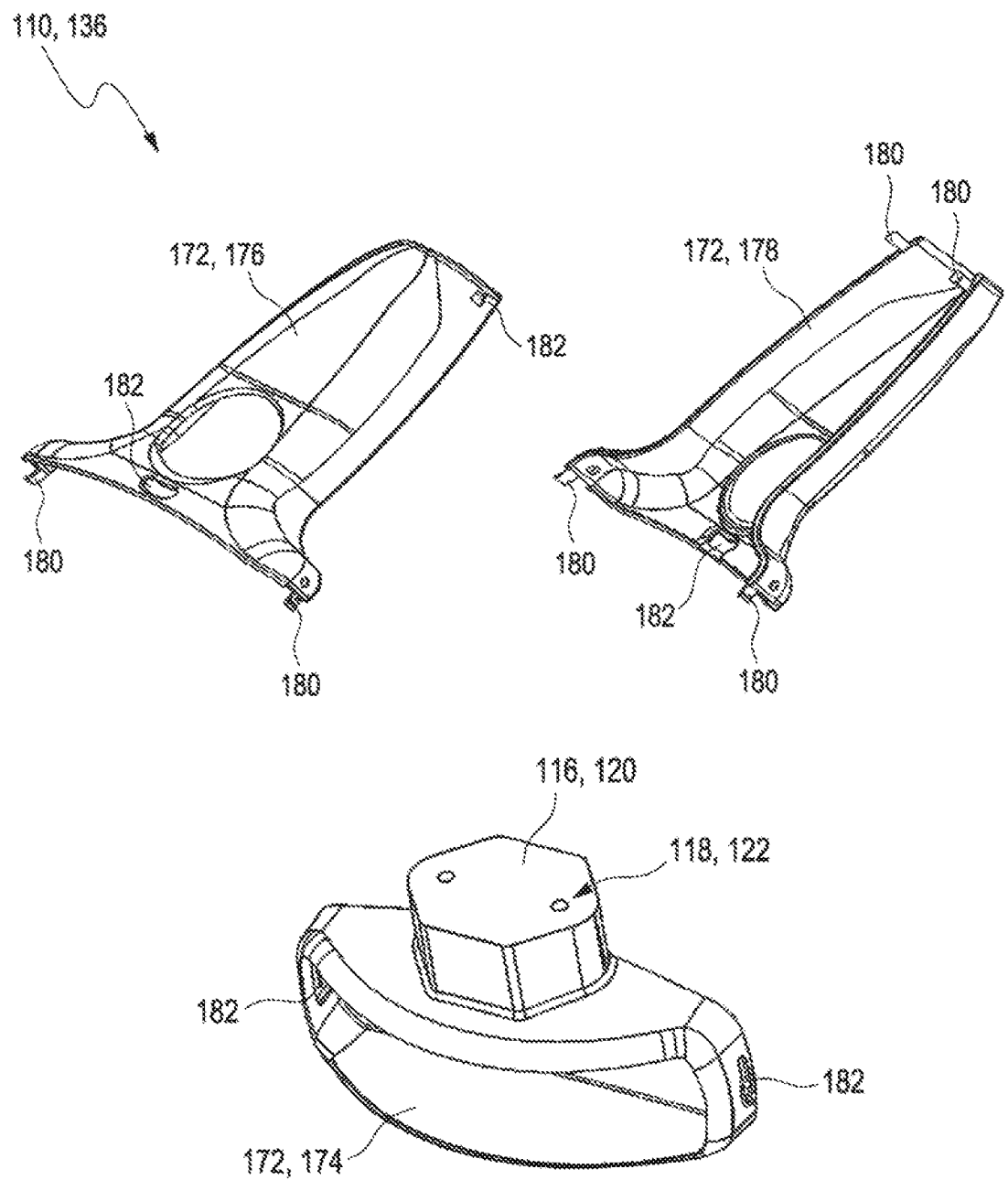
FIG. 8 shows a further embodiment of the mounting device.

In a further preferred embodiment shown in FIG. 8, the mounting device 110 may comprise at least two, preferably three, connectable parts 172, which, when connected, may at least partially reproduce the three-dimensional shape of the ultrasonic probe 114. This may be particularly advantageous for providing an ergonomic shape of the mounting device 110 and/or for providing a high stability of the connection between the mounting device 110 and the ultrasonic probe 114 and/or between the electromagnetic field generator 112 and the ultrasonic probe 114. In particular, the at least two parts 172 may be formed using a cast of the ultrasonic probe 114. Specifically, the at least two, preferably three, parts 172 may together form or may together comprise the second fastening structure 136. In particular, the connectable parts 172 may comprise a bottom cover 174, a front cover 176 and a back cover 178, as shown in FIG. 8. In particular, the connectable parts 172 may be connectable to one another with at least one snap-in mechanism mediated by at least one snap-in pin 180 and at least one corresponding snap-in hole 182. Other means and/or mechanisms for connecting the connectable parts 172 are also feasible.

According to another aspect of the present invention, a mounting system 168 is further schematically depicted in FIGS. 3A to 3C. The mounting system 168 comprises the mounting device 110. The mounting system 168 further comprises the electromagnetic field generator 112. The electromagnetic field generator 112 is attached within an envelope 121 of 5 cm of the ultrasonic probe 114 when mounted on the ultrasonic probe 114 by the mounting device. FIGS. 3A to 3C show different embodiments of the mounting system 168 in a partial view. The electromagnetic field generator 112 may have a dimension below 5 cm. Further, the electromagnetic field generator 112 may be cuboid-shaped, as shown in FIGS. 1, 2, 3A, 3B, 3C and 4. In particular, the cuboid-shaped electromagnetic field generator 112 may have an edge length of below 5 cm. By way of example, the electromagnetic field generator 112 may be cuboid-shaped having an edge length of 0.5 cm to 4.5 cm.

According to another aspect of the present invention, a mounting assembly 170 is further illustrated in FIGS. 1 and 2. The mounting assembly 170 comprises the mounting system 168. The mounting assembly 170 further comprises an ultrasonic probe 114. FIGS. 1 and 2 show examples of preferred embodiments of the mounting assembly 170. The mounting device 110, preferably the second fastening structure 136, more preferably the second fastening component 124, may be integrated into the housing 166 of the ultrasonic probe 114, as shown in FIG. 4.

According to another aspect of the invention, the ultrasonic probe 114 is further illustrated in FIG. 4, wherein the mounting device 110 is at least partially integrated into the housing 166 of the ultrasonic probe 114 as shown in FIG. 4.

LIST OF REFERENCE NUMBERS 110 mounting device
112 electromagnetic field generator
114 ultrasonic probe
116 mounting position
118 first fastening structure
120 predefined mounting position
121 envelope
122 first fastening component
124 second fastening component
126 male part of a press button
128 female part of a press button
129 snap-fit fastener
130 guide rail
132 indentation
134 protrusion
135 strap
136 second fastening structure
137 cable guide
138 first connection element
140 second connection element
142 bracket
144 hinge
146 screw
148 screw-nut
151 ring
152 connection position
154 predefined connection position
156 base of the ultrasonic probe
158 neck of the ultrasonic probe
160 base-neck transition of the ultrasonic probe
161 needle guide
162 layer of anti-slip material
164 adhesive strip
166 housing of the ultrasonic probe
168 mounting system
170 mounting assembly
172 connectable pant
174 bottom cover
176 front cover
178 back cover
180 snap-in pin
182 snap-in hole

The invention claimed is:

1. An assembly, comprising:
   an electromagnetic field generator;
   an ultrasonic probe; and
   a mounting device for reversibly mounting the electromagnetic field generator on the ultrasonic probe for orientating the electromagnetic field generator with respect to the ultrasonic probe in at least one mounting position, wherein the mounting device comprises at least one first fastening structure, wherein the mounting device is connectable to the electromagnetic field generator via the at least one first fastening structure, wherein the electromagnetic field generator is connectable to the ultrasonic probe within an envelope of 5 cm of the ultrasonic probe when mounted on the ultrasonic probe by the mounting device.

2. The assembly according to claim 1, wherein the mounting device is reversibly connectable to the ultrasonic probe.

3. The assembly according to claim 1, wherein the mounting device is arranged within an envelope of 5 cm of the ultrasonic probe.

4. The assembly according to claim 1, wherein the electromagnetic field generator is mountable on the ultrasonic probe in at least two mounting positions by the mounting device.

5. The assembly according to claim 1, wherein the at least one first fastening structure comprises at least one first fastening component configured to interact with at least one second fastening component.

6. The assembly according to claim 5, wherein the at least one first fastening component comprises at least one of at least one element selected from the group consisting of: a male part of a press fastener; a female part of a press fastener; a male part of a press button; a female part of a press button; a protrusion; an indentation; an elevation; a depression; a plug connector; a plug socket; a pin; a pinhole; a button; a button hole; a hook of a hook-and-loop fastener; a loop of a hook-and loop fastener; a clip; a guide rail; a sliding fastener; a snap-fit fastener; a pin fastener; a clutch; and a clamp.

7. The assembly according to claim 1, wherein the mounting device comprises at least one second fastening structure, wherein the mounting device is connectable to the ultrasonic probe via the at least one second fastening structure.

8. The assembly according to claim 7, wherein the at least one second fastening structure comprises at least one of at least one element selected from the group consisting of: a bracket, a belt; a ring; a tie; a male part of a press fastener;

a female part of a press fastener; a male part of a press button; a female part of a press button; a protrusion; an indentation; an elevation; a depression; a plug connector; a plug socket; a pin; a pinhole; a button; a button hole; a hook of a hook-and-loop fastener; a loop of a hook-and loop fastener; a clip; a guide rail; a sliding fastener; a snap-fit fastener; a pin fastener; a clutch; and a clamp.

9. The assembly according to claim 7, wherein the at least one second fastening structure is formed by a single piece or wherein the at least one second fastening structure comprises at least one first connection element and at least one second connection element, the mounting device being connectable to the ultrasonic probe via the at least one first connection element, the at least one second connection element being connectable to both the at least one first connection element and the at least one first fastening structure.

10. The assembly according to claim 9, wherein the at least one first connection element comprises at least one element selected from the group consisting of: a bracket; a belt; a ring; a tie; and a clip.

11. The assembly according to claim 9, wherein the at least one second connection element comprises the at least one second fastening component.

12. The assembly according to claim 11, wherein the at least one second fastening component comprises at least one of at least one element selected from the group consisting of: a male part of a press fastener; a female part of a press fastener; a male part of a press button; a female part of a press button; a protrusion; an indentation; an elevation; a depression; a plug connector; a plug socket; a pin; a pinhole; a button; a button hole; a hook of a hook-and-loop fastener; a loop of a hook-and loop fastener; a clip; a guide rail; a sliding fastener; a snap-fit fastener; a pin fastener; a clutch; and a clamp.

13. The assembly according to claim 7, wherein the at least one first fastening structure and the at least one second fastening structure are connectable via at least one connection selected from the group consisting of: a snap-fit connection; a press-button connection; a sliding connection; a clamp connection; a press-fastener connection; a button connection; a hook-and-loop connection; a pin connection; a clip connection; and a clutch connection.

14. The assembly according to claim 1, wherein the mounting device comprises at least two connectable parts which, when connected, at least partially reproduce a three-dimensional shape of the ultrasonic probe.

15. The assembly according to claim 1, wherein the mounting device comprises a further attachment element adapted for mounting an attachable instrument on the ultrasonic probe using the mounting device.

16. The assembly according to claim 15, wherein the attachable instrument is a needle guide.

17. The assembly according to claim 1, wherein the mounting device is at least partially integrated into a housing of the ultrasonic probe.

18. A mounting assembly comprising:
an ultrasonic probe; and
a mounting system comprising:
   an electromagnetic field generator; and
   a mounting device for reversibly mounting the electromagnetic field generator on the ultrasonic probe for orientating the electromagnetic field generator with respect to the ultrasonic probe in at least one mounting position, wherein the mounting device comprises at least one first fastening structure, wherein the mounting device is connectable to the electromagnetic field generator via the first fastening structure;
wherein the electromagnetic field generator is attached within an envelope of 5 cm of the ultrasonic probe when mounted on the ultrasonic probe by the mounting device.

19. The mounting assembly according to claim 18, wherein the mounting device is at least partially integrated into a housing of the ultrasonic probe.

20. The mounting assembly according to claim 18, wherein a second fastening structure is at least partially integrated into the housing of the ultrasonic probe.

21. An assembly, comprising:
an ultrasonic probe;
an electromagnetic field generator; and
a mounting device for reversibly mounting the electromagnetic field generator on the ultrasonic probe for orientating the electromagnetic field generator with respect to the ultrasonic probe in at least one mounting position, wherein the mounting device comprises at least one first fastening structure, wherein the mounting device is connectable to the electromagnetic field generator via the first fastening structure, wherein the mounting device is at least partially integrated into a housing of the ultrasonic probe;
wherein the electromagnetic field generator is at least partially integrated into the housing of the ultrasonic probe.

* * * * *